(12) United States Patent
Boesten et al.

(10) Patent No.: US 6,222,013 B1
(45) Date of Patent: Apr. 24, 2001

(54) PROCESS FOR ESTERIFICATION OF AMINO

(75) Inventors: Wilhelmus H. J. Boesten, Sittard; Peter J. L. M. Quaedflieg, Geleen, both of (NL)

(73) Assignee: DSM NV, Heerlen (NL)

( * ) Notice: Subject to any disclaimer, the term of this patent is extended or adjusted under 35 U.S.C. 154(b) by 0 days.

(21) Appl. No.: 09/425,023

(22) Filed: Oct. 25, 1999

Related U.S. Application Data

(63) Continuation of application No. PCT/NL98/00227, filed on Apr. 23, 1998.

(30) Foreign Application Priority Data

Apr. 25, 1997 (NL) .................................................. 1005901

(51) Int. Cl.$^7$ .................................................. C07K 1/00
(52) U.S. Cl. .................. 530/333; 530/338; 530/345; 560/1
(58) Field of Search ................................. 560/1; 530/333, 530/345

(56) References Cited

U.S. PATENT DOCUMENTS 5,424,476    6/1995    Takemoto ............................... 560/38

FOREIGN PATENT DOCUMENTS 0 544 205    6/1993    (EP) .

OTHER PUBLICATIONS

Chemical Abstracts, vol. 107, No. 13, Sep. 28, 1987, Columbus, Ohio, US; abstract No. 115953h. I. Rusev et al: "Esterification of alpha–amino carboxylic acids with monomethyl sulfate" p. 665; XP002050388 cited in the application see abstract & Khim. Ind., vol. 58, No. 10, 1986, pp. 445–447.

Chemical Abstracts, vol. 122, No. 7, Feb. 13, 1995, Columbus Ohio, US; abstract No. 51410w. A Wolksi et al.: "Method for preparation of the mothyl ester of 3–aminopyrazine–2–carboxylic acid" p. 1097; XP002050389 cited in the application see abstract & PL 159 729 A (Polfa) Jan. 29, 1993.

Chemical Abstracts, vol. 119, No. 11, Sep. 13, 1993, Columbus, Ohio, US; abstract No. 117812h. R. A. El–Sayed et al: "Some new reactions of cinnamoylmorpholine derivatives with amino acids" p. 999; XP002050390 see abstract & Pak. J. Sci. Ind. Res., vol. 35, No. 11, pp. 434–437.

*Primary Examiner*—Christopher S. F. Low
*Assistant Examiner*—David Lukton
(74) *Attorney, Agent, or Firm*—Pillsbury Madison & Sutro LLP

(57) ABSTRACT

A process is disclosed for the esterification of an amino acid or peptide in which the amino acid or peptide is converted into the corresponding ester in the presence of a hydrosulphate have the general formula $ROSO_3H$, where R represents an alkyl group, with the hydrosulphate being prepared, in the presence of the amino acid or peptide, from chlorosulphonic acid and an alcohol having the general formula ROH, where R has the same meaning as above. The chlorosulphonic acid to amino acid or peptide molar ratio preferably is between 0.8 and 2.0, in particular between 1.0 and 1.3. A primary alcohol, in particular methanol, is preferably used as alcohol. The amino acid used may be for example an α-amino acid chosen from the group comprising p-hydroxyphenylglycine, phenylglycine, phenylalanine, tyrosine, proline and valine; L-alanyl-L-proline or an ester of L-aspartyl-L-phenylalanine, for example, may be used as peptide.

9 Claims, No Drawings

PROCESS FOR ESTERIFICATION OF AMINO

This appln is a cont of PCT/NL98/00227 filed Apr. 23, 1998.

The invention relates to a process for the esterification of an amino acid or peptide in which the amino acid or peptide is converted into the corresponding ester in the presence of a monoalkyl hydrosulphate having the general formula $ROSO_3H$, where R represents an alkyl group.

A similar process is known from Khim. Ind (Sofiya), 58(10), 445–7, 1986, which describes the esterification of aliphatic amino acids with the aid of methylhydrosulphate.

A drawback of the known process is that in theory at least 2 equivalents of methylhydrosulphate are required for the esterification and in experiments even 3.75 equivalents to achieve a yield of 93–94% while the reaction time required for this is relatively long.

The invention provides a process for the esterification of amino acids and peptides that does not have the aforementioned drawbacks.

This is achieved according to the invention in that the hydrosulphate is prepared, in the presence of the amino acid or peptide, from chlorosulphonic acid and an alcohol having the general formula ROH, where R has the same meaning as above.

Suprisingly, it has been found that a conversion higher than 99% can be achieved, in a reaction time of less than an hour, using a substantially equimolar amount of chlorosulphonic acid calculated with respect to the amount of aminoacid or peptide. Contrary to expectations, no reaction was found to take place between the amino function of the amino acid or peptide and chlorosulphonic acid to form the corresponding N-substituted amidosulphonic acid. Another important advantage of the process according to the invention is that the reaction can be carried out at high amino acid or peptide concentrations in alcohol and that high ester concentrations proved possible.

While it is true that PL-B-159729 discloses an esterification in a methanol solution which contains methylhydrosulphate ($CH_3OSO_3H$), with the methylhydrosulphate being formed in situ from methanol and chlorosulphonic acid, the said patent publication describes the esterification of 3-amino-pyrazine-2-carboxylic acid. Besides the fact that the said patent publication deals with a fundamentally different compound, it claims that the esterification requires in theory at least 2 equivalents of chlorosulphonic acid ($ClSO_3H$), 4 equivalents of chlorosulphonic acid being needed in experiments, and the reaction time amounting to many hours.

In principle, all amino acids and peptides, which may be optically active, for example dipeptides, can be esterified by the process according to the invention, for example α-amino acids, both aromatic and aliphatic, in particular phenylglycine, which may or may not be substituted, for example p-hydroxyphenylglycine, phenylalanine, tyrosine, proline and valine. The hydroxy function of for example-hydroxyphenylglycine, too, proved not to react with chlorosulphonic acid. Known dipeptides are for example L-alanyl-L-proline (AlaPro) or L-aspartyl-L-phenylalanine methyl ester (APM). It has been found that essentially no racemisation occurred in the esterification of optionally active compounds.

An alcohol use may in principle be made of any alcohol which may normally be used for acid-catalysed esterification, for example alcohols having the formula ROH, where R represents an alkyl group, in particular an alkyl group having 1–20 C atoms. Preferably, use is make of alcohols having the formula ROH, where R represents an alkyl group, in particular a lower alkyl group having 1–5 C atoms, for example methanol, ethanol, (i- or n-)propanol, (i- or n-)-butanol. Particularly good results are achieved with primary alcohols.

The temperature at which the esterification reaction takes place is not particularly critical and in practice usually lies between 30° C. and the reflux temperature, preferably between 50° C. and 120° C. The optimum temperature may vary depending on the desired ester, that is, the applied alcohol and amino acid or peptide. It has been found that the formation of the methyl ester usually proceeds optimally at the reflux temperature, whereas a temperature somewhat lower than the reflux temperature often gives better results for the higher alkyl esters. The optimum temperature can readily be determined by those skilled in the art.

Any inert, organic solvent can be used as solvent (or suspending agent) in the process according to the invention. It is preferred for the alcohol employed in the esterification to be used as a solvent.

The chlorosulphonic acid to amino acid or peptide molar ration preferably is between 0.8 and 2.0, in particular, a (slightly) more than equimolar ratio of chlorosulphonic acid to amino acid or peptide is chosen, for example between 1.0 and 1.3.

In a suitable embodiment of the process according to the invention the amino acid or peptide to be esterified is suspended or dissolved in the alcohol. Subsequently, chlorosulphonic acid is added, preferably metered drop-wise for a period of for example 2–20 minutes, preferably 4–10 minutes, to this solution, optionally with cooling it the temperature is not to rise directly to the reflux temperature or the envisages esterification temperature. Subsequently, the temperature is raised to the desired level, for example between 50 and 120° C. and the reaction mixture is kept at this temperature for a period of for example between 10 minutes and 10 hours depending on the temperature and the desired ester. When the conversion is (virtually) complete the ester is recovered, for example by evaporating the alcohol and extraction at increased pH using an (in essence commonly known) organic solvent that is immiscible or poorly miscible with water, for example toluene, dichloromethane or methylisobutylketone (MIBK). In some cases, for example in the case of the esters of p-hydroxyphenylglycine, it will also be possible to recover the ester directly via crystallization from water at increased pH (pH 8–10), whether or not after completely or partially evaporating the alcohol.

The invention is now illustrated by the examples without being limited thereto.

EXAMPLES

General Procedure

Esterification reaction

A suspension or solution of 30 wt. % amino acid or dipeptide in the alcohol was cooled in an ice bath to 0–5° C. under a continuous nitrogen stream. Next, 1.1 equivalent of $ClSO_3H$ was added drop-wise, the ice bath was removed and the reaction mixture was brought to the desired temperature.

Determination of conversion

A sample was taken from the reaction vessel from time to time, carefully weighed and diluted by a factor of 3 (on a weight basis) with the alcohol used. For each reaction studied standard solutions of the amino acid that corresponded with 90, 95, 98 and 99% conversion were carefully made. In this way, 2 μl amounts of (carefully diluted) samples of the reaction mixture were separated with the aid of TLC simultaneously with 2-μl amounts of the aformentioned standard solutions. After spraying with ninhydrin, the measured intensities of the amino acid spots were compared and conversion (in %) could be estimated fairly accurately. The maximum values are cited in the examples as the conversion (conv.); the time (t) it took to achieve maximum conversion is given in the next column.

Working up

In a number of examples the mixture obtained was worked up. In those cases a value is stated for the yield (yld), which refers to the yield after working up. The following working-up techniques were used.

The mixture was obtained after the esterification reaction was concentrated by evaporation whereupon the residue was divided between dichloromethane and water and the resulting mixture was slowly raised to pH=9 with the aid of 5 N aqueous NaOH with vigorous stirring. The layers were separated and the aqueous layer was extracted once again with dichloromethane. The combined organic phase was dried (NaSO$_4$) and concentrated by evaporation, in which process the free ester was obtained.

The obtained esters of L-tyrosine and D/L-p-hydroxyphenylglycine were worked up via crystallization, with the reaction mixture obtained after the esterification being concentrated. The residue was absorbed in water, cooled to about 5° C. and neutralized with 5 N aqueous NaOH to pH=10–11, which resulted in crystallization of the free ester. After additional stirring at 5° C. for about 15 minutes the precipitate was filtered out and washed twice with water. The resulting solid was vacuum-dried (40° C.) until its weight ceased to decrease. In all cases, a >99% pure ester was recovered ($^1$H NMR, HPLC) after working up.

EXAMPLES I TO IV p Methylation of amino acids (a.a.)

L-phenylalanine (L-Phe), L-tyrosine (L-Tyr), L-proline (L-Pro) and D/L-p-hydroxyphenylglycine ((D/L-HPG) were esterified with methanol (MeOH) using the general procedure. The results are shown in Table 1.

TABLE 1

| Ex  | a.a.    | alcohol | T         | conv. | t       | yld |
|-----|---------|---------|-----------|-------|---------|-----|
| I   | L-Phe   | MeOH    | 69–75° C. | >99%  | 30 min. | 94% |
| II  | L-Tyr   | MeOH    | 69–75° C. | >99%  | 20 min. | 83% |
| III | L-Pro   | MeOH    | 69–75° C. | 98%   | 35 min. | —   |
| IV  | D/L-HPG | MeOH    | 69–75° C. | >99%  | 30 min. | 95% |

EXAMPLES V TO XVIII

Esterification of amino acids with alcohols other than methanol

The same amino acids as in Examples I to IV were now esterified in the same way with other alcohols: ethanol (EtOH), n-propanol (n-PrOH), i-propanol (i-PrOH), n-butanol (n-BuOH), i-butanol (i-BuOH). The results are shown in Table 2.

TABLE 2

| Ex.   | a.a   | alcohol | T           | conv.   | t       | yld. |
|-------|-------|---------|-------------|---------|---------|------|
| V     | L-Phe | EtOH    | 80–86° C.   | 95%     | 30 min. | —    |
| VI    | L-Tyr | EtOH    | 80–86° C.   | 95%     | 30 min. | —    |
| VII   | L-Pro | EtOH    | 80–86° C.   | 90%     | 15 min. | —    |
| VIII  | L-Phe | EtOH    | 60° C.      | >98%    | 5 h     | —    |
| IX    | L-Tyr | EtOH    | 60° C.      | >98%    | 5 h     | 82%  |
| X     | L-Pro | EtOH    | 60° C.      | 97%     | 1 h     | —    |
| XI    | L-Tyr | n-PrOH  | 97–101° C.  | 93%     | 1 h     | —    |
| XII   | L-Tyr | n-BuOH  | 111–114° C. | 92%     | 40 min. | —    |
| XIII  | L-Tyr | i-BuOH  | 103–105° C. | 92%     | 45 min. | —    |
| XIV   | L-Tyr | i-PrOH  | 82–86° C.   | 80–85%  | 3 h     | —    |
| XV    | L-Tyr | n-PrOH  | 65° C.      | >98%    | 6 h     | 94%  |
| XVI   | L-Tyr | n-BuOH  | 65° C.      | >98%    | 6 h     | 96%  |
| XVII  | L-Try | i-BuOH  | 65° C.      | >98%    | 5 h     | 96%  |
| XVIII | L-Tyr | i-PrOH  | 65° C.      | 90%     | 24 h    | 78%  |

EXAMPLES XIX TO XXII

Esterification of dipeptides with methanol

L-alanyl-L-proline (Ala-Pro) and L-aspartyl-L-phenylalanine methyl (APM) were esterified by the aformentioned general procedure. The results are shown in Table 3.

TABLE 3

| Ex.  | a.a.    | alcohol | T         | conv. | t       |
|------|---------|---------|-----------|-------|---------|
| XIX  | Ala-Pro | MeOH    | 50° C.    | >99%  | 20 min. |
| XX   | Ala-Pro | MeOH    | 69–75° C. | >99%  | 10 min. |
| XXI  | APM     | MeOH    | 69–75° C. | >99%  | 2 h     |

What is claimed is:

1. A process for esterifying an amino acid or peptide comprising the step of combining the amino acid or peptide to be esterified, an alcohol of the formula ROH, wherein R is an alkyl group, and chlorosulfonic acid,
   whereby in said process the alcohol reacts with the chlorosulfonic acid to form a hydrosulfate of the formula ROSO$_3$H, and subsequently the hydrosulfate reacts with the amino acid or peptide to form the corresponding amino acid ester or peptide ester.

2. A process according to claim 1, wherein said chlorosulfonic acid and said amino acid or peptide are used at a molar ration between 0.8 and 2.0.

3. A process according to claim 2, wherein said molar ration is between 1.0 and 1.3.

4. A process according to any on of claims 1–3, wherein said alcohol is a primary alcohol.

5. A process according to claim 4, wherein said alcohol is methanol.

6. A process according to any one of claims 1–3, wherein in said process hydrosulphate is prepared by adding said chlorosulphonic acid to a suspension or solution of the amino acid or peptide in the alcohol.

7. A process according to claim 6, wherein said chlorosulfonic acid is metered in said suspension or said solution.

8. A process according to any one of claims 1–3, wherein said amino acid used is an α-amino acid selected from the group consisting of p-hydroxyphenylglycine, phenylhlycine, phenylalanine, tyrosine, proline and valine.

9. A process according to any one of claims 1–3, wherein said process said peptide used is L-alanyl-L-proline or mono-ester of L-aspartyl-L-phenylalanine.

* * * * *